United States Patent [19]

Blank et al.

[11] Patent Number: 5,179,211

[45] Date of Patent: Jan. 12, 1993

[54] PROCESS FOR THE PREPARATION OF INDOLES

[75] Inventors: Heinz U. Blank, Odenthal-Gloebusch; Friedrich-Wilhelm Ullrich, Cologne; Karlheinrich Meisel, Odenthal-Osenau; Willi Streicher, Cologne; Nikolaus Schulz, Kuerten; Dieter Irmscher, Bergisch Gladbach; Günther Klag, Leverkusen, all of Fed. Rep. of Germany

[73] Assignee: Bayer Aktiengesellschaft, Leverkusen, Fed. Rep. of Germany

[21] Appl. No.: 792,317

[22] Filed: Nov. 13, 1991

[30] Foreign Application Priority Data

Nov. 21, 1990 [DE] Fed. Rep. of Germany ....... 4037004

[51] Int. Cl.$^5$ ............................................ C07D 209/04
[52] U.S. Cl. ............................................ 548/508
[58] Field of Search ............................................ 548/508

[56] References Cited

U.S. PATENT DOCUMENTS 3,639,420  1/1972  Illy et al. ............................ 548/508
4,057,530 11/1977  Pigerol et al. ...................... 548/508
4,062,865 12/1977  Moggi ................................. 548/508

FOREIGN PATENT DOCUMENTS 574840    4/1933  Fed. Rep. of Germany ...... 548/508
1906832  11/1969  Fed. Rep. of Germany ...... 548/508

OTHER PUBLICATIONS

CA 94:174800j Fischer indole . . . 3-alkoxycarbonylindoles, Mills et al. p. 700, 1981.
CA 110:145047v Photochromic . . . derivatives. Iriyo et al. 1989 p. 675.
The Journal of Organic Chemistry, vol. 33, No. 11, Nov. 1968, pp. 4283-4285 Illy et al.
R. K. Brown in the Chemistry of Heterocyclic Compounds, vol. 25, Part one: Indoles, Chapter II, 1972, pp. 246-258.
Chemiken-Zeitung, 22 (1988), 37, Plancher, Synthesis . . . Indden.
J. Org. Chem., vol. 42, No. 14, 1977, pp. 2474-2480, Annelation of Pyridinium . . . Heterocycles, Chapman et al.
J. Am. Chem. Soc., 74 (1952), 3948 Fisher Indole Synthesis . . . Acid, Kissman et al.
Chemistry and Industry, Mar. 13, 1965, p. 473, Fischer Indole Synthesis and Ethylation of 2,3-Disubstituted Indoles with Polyphosphate Esters, by Y. Kanaoka et al.

Primary Examiner—Mary C. Lee
Assistant Examiner—Joseph K. McKane
Attorney, Agent, or Firm—Sprung Horn Kramer & Woods

[57] ABSTRACT

Indoles of the formula

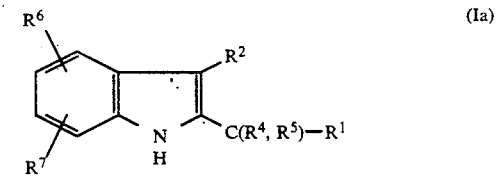

(Ia)

or

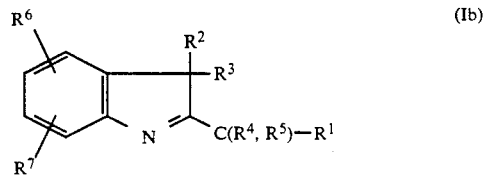

(Ib)

can be prepared by reaction of a phenylhydrazine of the formula

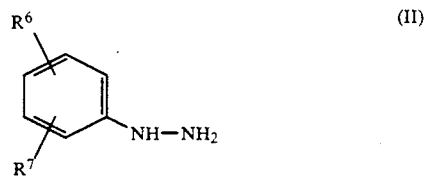

(II)

which is unsubstituted in at least one ortho-position, with a ketone of the formula

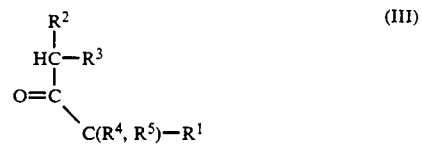

(III)

in an aqueous medium in the presence of an acid compound, less than 5 equivalents, based on 1 mol of phenylhydrazine, of an acid compound having a pK value of 1.3-4.5 being employed.

17 Claims, No Drawings

PROCESS FOR THE PREPARATION OF INDOLES

BACKGROUND OF THE INVENTION

The present invention relates to a process for the preparation of indoles by cyclisation of phenylhydrazones, which are formed from phenylhydrazine and ketones, in the presence of less than 5 equivalents of an acid compound having a pK value of 1.3–4.5.

Indoles are important intermediates in the dyestuffs industry. It is known to cyclise phenylhydrazones in organic media using Lewis acids or protonic acids, for example in ethanol in the presence of zinc chloride (Chem.-Zeitg. 22 (1898), 38), in glacial acetic acid as the reaction medium (J. Org. Chem. 42 (1977), 2474) or in chloroform in the presence of polyphosphoric acid esters (Chem. and Ind. 1965, 473). Furthermore, a reaction of this type in polyphosphoric acid without further addition of solvent has been described (J. Am. Chem. Soc. 74 (1952), 3948).

It is also known to carry out this reaction in an aqueous medium using Broensted acids, in which case, however, an acid having a pK value of below 1.3 has to be employed (German Offenlegungsschrift 19 06 832; J. Org. Chem. 33 (1968), 4283).

It has now been found, surprisingly, that the indole synthesis in an aqueous reaction medium can also be carried out in short reaction times with good yields using acid compounds having a pK value of 1.3 and above, less than 5 equivalents of this acid compound, relative to the phenylhydrazine, being employed. This is the more surprising since it is known from German Offenlegungsschrift 19 06 832 that when substituted aliphatic or aromatic acids having a pK value in the vicinity of 1.3 are used large amounts of acid and long reaction times are required in order to achieve satisfactory yields.

SUMMARY OF THE INVENTION

A process has been found for the preparation of 1-H- or 3-H-indoles of the formula

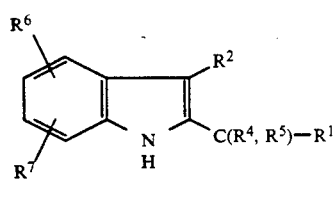
(Ia)

or

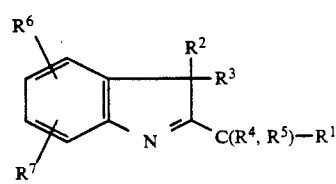
(Ib)

by reaction of a phenylhydrazine of the formula

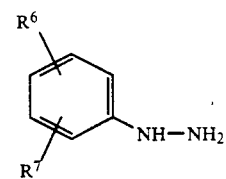
(II)

which is unsubstituted in at least one ortho-position, with a ketone of the formula

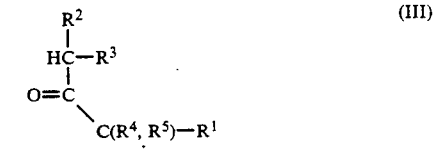
(III)

in an aqueous medium in the presence of an acid compound, where, in the formulae, $R^1$ represents hydrogen or straight-chain or branched $C_1$–$C_4$-alkyl, which can be substituted by halogen, cyano or $CON(R^8,R^9)$, $R^2$ and $R^3$ independently of one another denote hydrogen, straight-chain or branched $C_1$–$C_{12}$-alkyl, which can be substituted by halogen, cyano or $CON(R^8,R^9)$, $C_5$–$C_6$-cycloalkyl or benzyl, at least one of the radicals $R^2$ and $R^3$ differing from hydrogen and it also being possible for $R^2$ and $R^3$ together to be $C_4$–$C_6$-alkylene or for $R^2$ and $R^1$ together to be $C_3$–$C_5$-alkylene, $R^4$ and $R^5$ independently of one another denote hydrogen or straight-chain or branched $C_1$–$C_4$-alkyl, which can be substituted by halogen, $R^6$ and $R^7$ independently of one another represent hydrogen, straight-chain or branched $C$ -$C_z$-alkyl, straight-chain or branched $C_1$–$C_4$-alkoxy, phenyl, phenoxy, halogen, hydroxyl, nitro, cyano or $N(R^8,R^9)$, it being possible for $R^6$ additionally to denote $CON(R^8,R^9)$, $COR^8$ or $COOR^8$, and $R^8$ and $R^9$ independently of one another represent hydrogen or straight-chain or branched $C_1$–$C_4$-alkyl, which process is characterised in that less than 5 equivalents, based on 1 mol of phenylhydrazine, of an acid compound having a pK value of 1.3–4.5 are employed.

Preferentially, a phenylhydrazine having at least one unsubstituted ortho-position, of the formula

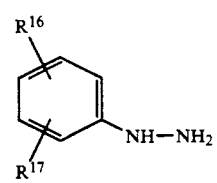
(IV)

is employed, wherein $R^{16}$ and $R^{17}$ independently of one another denote hydrogen, straight-chain or branched $C_1$–$C_4$-alkyl, straight-chain or branched $C_1$–$C_4$-alkoxy, phenyl, phenoxy, halogen, hydroxyl, cyano or $N(R^{18},R^{19})$, $R^{18}$ and $R^{19}$ independently of one another representing hydrogen, methyl or ethyl.

Particularly preferably, a phenylhydrazine having at least one unsubstituted ortho-position, of the formula

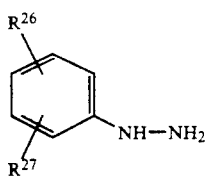

is employed, wherein $R^{26}$ and $R^{27}$ independently of one another denote hydrogen, methyl, ethyl, methoxy, ethoxy or halogen and $R^{26}$ additionally can denote hydroxyl or $N(R^{18}, R^{19})$.

In a further preferred manner, a ketone of the formula

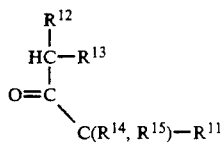

is employed, wherein $R^{11}$ represents hydrogen or methyl or ethyl, each of which can be substituted by halogen, $R^{12}$ and $R^{13}$ independently of one another denote hydrogen, straight-chain or branched $C_1$-$C_4$-alkyl, which can be substituted by halogen, or benzyl, at least one of the radicals $R^{12}$ and $R^{13}$ differing from hydrogen, and $R^{14}$ and $R^{15}$ independently of one another denote hydrogen or methyl or ethyl, each of which can be substituted by halogen.

In a further particularly preferred manner, a ketone of the formula

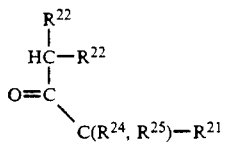

is employed, wherein $R^{21}$, $R^{22}$, $R^{23}$, $R^{24}$ and $R^{25}$ independently of one another denote hydrogen or methyl or ethyl, each of which can be substituted by halogen, at least one of the radicals $R^{22}$ and $R^{23}$ differing from hydrogen.

Halogen which may be mentioned is fluorine, chlorine or bromine, preferably fluorine or chlorine.

Straight-chain or branched $C_1$-$C_4$-alkyl which may be mentioned is, for example, methyl, ethyl, propyl, isopropyl, butyl, isobutyl or tert-butyl. Preferred alkyl is methyl or ethyl.

The following may also be mentioned by way of example as straight-chain or branched $C_1$-$C_{12}$-alkyl, in addition to the said $C_1$-$C_4$-alkyl: the isomeric pentyls, hexyls, octyls, decyls and dodecyls. Within the framework of the radicals $R^2$ and $R^3$, long-chain alkyl of this type preferably has 1-8 C atoms and particularly preferentially has 1-4 C atoms Alkyl substituted by halogen is, for example, chloromethyl, dichloromethyl, trichloromethyl, fluoromethyl, difluoromethyl, trifluoromethyl, bromomethyl, dibromomethyl, tribromomethyl, the mixed chlorinated/fluorinated methyls, the mixed halogenated methyls involving bromine or involving all three halogens mentioned, and the corresponding partially or completely halogenated ethyls, propyls, butyls and their branched isomers. The various alkylene chains having 3-6 C atoms are trimethylene, tetramethylene, pentamethylene or hexamethylene.

Straight-chain or branched alkoxy is, for example, methoxy, ethoxy, propoxy, isopropoxy, butoxy, isobutoxy or tert-butoxy.

At least one of the radicals $R^2$ and $R^3$ or $R^{12}$ and $R^{13}$ or $R^{22}$ and $R^{23}$ always differs from hydrogen For the case where $R^3$ is hydrogen, the 1-H-indoles are formed in the process according to the invention; for the case that none of the radicals $R^2$ and $R^3$ or $R^{12}$ and $R^{13}$ or $R^{22}$ and $R^{23}$ is hydrogen, the corresponding 3-H-indoles form Suitable phenylhydrazines for the process according to the invention are:

phenylhydrazine, 4-methylphenylhydrazine, 4-dodecylphenylhydrazine, 2,5-dimethylphenylhydrazine, 3,4-dimethylphenylhydrazine, 4-methoxyphenylhydrazine, 4hydroxyphenylhydrazine, 4-chlorophenylhydrazine, 5-chloro-2-methylphenylhyirazine and 2,4-dichlorophenylhydrazine.

Suitable ketones for the process according to the invention are:

butan-2-one, 3-methylbutan-2-one, pentan-3-one, 4-methylpentan-2-one, cyclohexanone, 2-methylcyclohexanone and dodecan-2-one.

An essential characteristic of the process according to the invention is that it is carried out in the presence of an acid compound having a pK value of 1.3-4.5, whereas the processes known hitherto used strong acids, for example sulphuric acid or hydrochloric acid, which have a pK value which in some cases is considerably lower than 1.3. Suitable acid compounds of this type are acid alkali metal salts and acid ammonium salts, such as sodium hydrogen sulphate or primary alkali metal phosphates; furthermore, weak inorganic acids or organic acids which are stronger than acetic acid but have a pK value of 1.3-4.5 can be employed Preferably, acid alkali metal salts or acid ammonium salts, preferably acid sodium salts, are employed Particularly preferentially, sodium hydrogen sulphate is employed.

Acid compounds of this type are employed in an amount of less than 5 equivalents per 1 mol of the phenylhydrazine employed, preferably in an amount of 1-4.9 equivalents, particularly preferentially 1.5-4.5 equivalents and very particularly preferentially 2-4 equivalents.

The process according to the invention is carried out at a temperature of 50°-150°, preferably 80°-110° C.

In the process according to the invention it is possible initially to introduce either the phenylhydrazine or the ketone, in each case together with the acid compound, in the aqueous medium, to bring the mixture to the reaction temperature and then to add the reactant which is still missing. It is frequently advantageous initially to introduce the phenylhy-drazine. It is also possible to add the phenylhydrazine and the ketone simultaneously to the aqueous medium which is at the reaction temperature and contains the acid compound; in this case also it can be advantageous initially to introduce a little phenylhydrazine and then to add the two components simultaneously. The simultaneous addition is also suitable for a continuous operation. In all cases, the formation of the phenylhydrazone and its cyclisation to give the indole, with elimination of $NH_3$, take place in immediate succession.

Of course, a separately prepared phenylhydrazone can also be reacted according to the invention.

After the termination of the process according to the invention, the reaction mixture is neutralised. On neutralisation, the indole is obtained as organic phase; if required, the indole can be further purified in a manner well known to those skilled in the art. The salt-containing aqueous phase, which is obtained at the same time during neutralisation, is disposed of in a known manner. This salt load requiring disposal is smaller in the process according to the invention than in the case of conventional indole syntheses.

A particularly advantageous variant of the process according to the invention is that a phenylhydrazine is employed which is prepared from the associated alkali metal phenylhydrazodisulphonate and/or the associated alkali metal phenylhydrazo-β-sulphonate by addition of sulphuric acid. This preparation generally takes place in the presence of residual alkali metal sulphite and/or alkali metal hydrogen sulphite, which had been employed to form the hydrazosulphonates. In a particularly advantageous manner, the required amount of sulphuric acid for the use of such a phenylhydrazine is adjusted such that, from the residual alkali metal sulphite, alkali metal hydrogen sulphite and the sulphate eliminated from the hydrazosulphonate, in total less than 5 equivalents of acid compound in the form of hydrogen sulphate are present per mole of phenylhydrazine.

The ketone is then added to such a phenylhydrazine, which contains the indicated amount of acid compound, and the process according to the invention is carried out as described in more detail above.

In a particularly preferred variant of the process according to the invention, recourse is made to the surprising possibility that the elimination of sulphate from the hydrazosulphonate can already be effected in the presence of the ketone required for the indole synthesis. In this case both the formation of the phenylhydrazine and its further reaction to give the indole take place in the same reaction mixture.

In a yet further advantageous variant of the process according to the invention, this surprising finding is extended to the extent that an aniline, of the formula

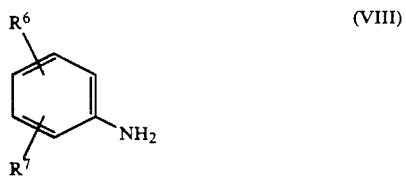

(VIII)

which is unsubstituted in at least one ortho-position and wherein $R^6$ and $R^7$ have the meaning indicated above, is used as the starting material for the preparation, according to the invention, of the indole and the reaction steps of diazotisation, reduction of the diazonium salt by means of sulphite, elimination of the sulphonate group and the final step of the reaction of the phenylhydrazine, thus obtained, with the ketone are carried out without isolation of the intermediates.

These advantageous variants of the process according to the invention which have been described are accompanied by a further considerable reduction in the salt load. Furthermore, there is no burden on the effluent by the phenylhydrazine, which is now no longer isolated as an intermediate. This is particularly significant since the phenylhydrazine has a considerable solubility in water, which, on the one hand, leads to a poorer total yield in the case of conventional intermediate isolation and, on the other hand, leads to burdening from the standpoint of industrial hygiene since the phenylhydrazines are regarded as carcinogenic If it were desired to suppress the solubility of phenylhydrazine in water in order to minimise its losses and to reduce the reservations with regard to industrial hygiene, the phenylhydrazine would have to be precipitated in the form of its salt with a large excess of mineral acid, which would likewise lead to a burden on the effluent. These problems which have been described are overcome according to the invention.

EXAMPLE 1

2 mol of methyl isopropyl ketone phenylhydrazone were added dropwise in the course of 30 min to a warm solution, at 90° C., of 5 mol of sodium hydrogen sulphate in 1900 ml of water The mixture was stirred for 3 h at 90° to 100° C. After cooling, the batch was neutralised and the organic phase was separated off and distilled. 286.7 g of 98.1% pure 2,3,3-trimethylindolenine were obtained. Yield: 88.3% of the theoretical yield.

EXAMPLE 2

226 g (2 mol) of phenylhy-drazine (95.7% pure) were initially introduced at 90° C. in a solution of 5 mol of sodium hydrogen sulphate in 1900 ml of water. 225 ml (2.1 mol) of methyl isopropyl ketone were added dropwise in the course of 30 min. The mixture was stirred for 3 h at 90° to 100° C. After cooling, the batch was neutralised and the organic phase was separated off and distilled. 299.3 g of 97.5% pure 2,3,3-trimethylindolenine were obtained Yield: 91.6% of the theoretical yield.

EXAMPLE 3

An aqueous benzenediazonium chloride solution prepared by conventional methods from 2 mol of aniline, 4.2 mol of hydrochloric acid and 2.02 mol of sodium nitrite was reacted in accordance with known processes with 5.2 mol of a mixture of sodium sulphite and sodium bisulphite to give a phenyl hydrazodisulphonate solution. 150 ml of 48% strength sulphuric acid (1 mol) were added dropwise to this solution at 80° C. The mixture was stirred for 2 h at 80° C. and 225 ml (2.1 mol) of methyl isopropyl ketone were then metered in in the course of 30 min. After a reaction time of 3 h at 95° to 100° C., the mixture was cooled. The batch was neutralised and the organic phase was separated off and distilled 276.3 g of 98.6% pure 2,3,3-trimethylindolenine were obtained Yield: 85.5% of the theoretical yield, based on aniline.

EXAMPLE 4

Aniline was reacted with methyl ethyl ketone in the same way as in Example 3. 2,3-Dimethylindole was formed in a yield of 93% of the theoretical yield.

EXAMPLE 5

Aniline was reacted with methyl isobutyl ketone in the same way as in Example 3. 3-Isopropyl-2-methylindole was formed in a yield of 86% of the theoretical yield.

EXAMPLE 6

Aniline was reacted with cyclohexanone in the same way as in Example 3. Tetrahydrocarbazole was formed in a yield of 87% of the theoretical yield.

EXAMPLE 7 p-Toluidine was reacted with methyl isopropyl ketone in the same way as in Example 3. 2,3,3,5-Tetramethyl-3-H-indole was formed in a yield of 87% of the theoretical yield.

EXAMPLE 8 p-Chloroaniline was reacted with methyl isopropyl ketone in the same way as in Example 3. 2,3,3-Trimethyl-5-chloro-3-H-indole was formed in a yield of 86% of the theoretical yield.

EXAMPLE 9

In a continuous reaction aniline was diazotised with hydrochloric acid and sodium nitrite in a molar ratio of 1:2.3:1.07.

This diazonium salt solution was reacted, likewise continuously, with 2.55 mol of sodium sulphite/sodium bisulphite mixture per mole of aniline to form a phenylhydrazodisulphonate solution. A portion of this mixture, corresponding to 1.91 mol of aniline, was added dropwise at 80° C. to 200 ml of a 48% strength sulphuric acid (1.35 mol). After a reaction time of 2 h at 80° C., 225 ml (2.1 mol) of methyl isopropyl ketone were metered in in the course of 30 min. After a reaction time of 3 hours at 95° to 100° C., the mixture was cooled. The batch was neutralised and the organic phase was separated off and distilled. 273.8 g of 98.2% pure 2,3,3-trimethylindolenine were obtained. Yield: 88.4% of the theoretical yield, based on aniline.

EXAMPLE 10

Phenylhydrazine was reacted with heptan-2-one in the same way as in Example 2. 2-Methyl-3-butylindole was formed in a yield of 38%.

EXAMPLE 11

27 g (0.25 mol) of phenylhydrazine were initially introduced at 90° C. in a solution of 1.12 mol of sodium hydrogen sulphate in 420 ml of water. 30 g (0.263 mol) of heptan-2-one were metered in in the course of 30 min. This mixture was stirred for 7 h at 100° C. After cooling, the batch was neutralised and the organic phase was separated off and distilled. 2-Methyl-3-butylindole was obtained in a yield of 62%.

What is claimed is:

1. A process for the preparation of 1-H- or 3-H-indoles of the formula

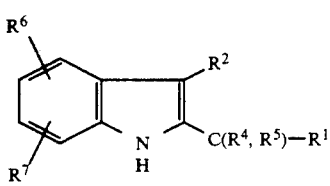

or

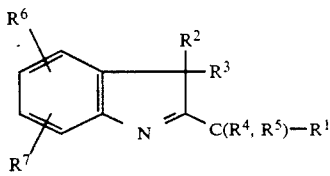

by reaction of a phenylhydrazine of the formula

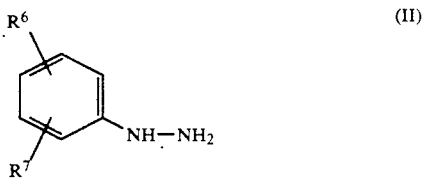

which is unsubstituted in at least one ortho-position, with a ketone of the formula

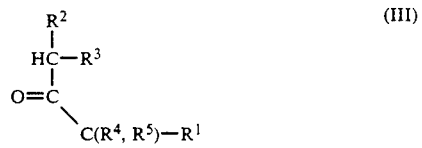

in an aqueous medium in the presence of an acid compound, where, in the formulae, $R^1$ represents hydrogen or straight-chain or branched $C_1$–$C_4$-alkyl, which can be substituted by halogen, cyano or $CON(R^8,R^9)$, $R^2$ and $R^3$ independently of one another denote hydrogen, straight-chain or branched $C_1$–$C_{12}$-alkyl, which can be substituted by halogen, cyano or $CON(R^8,R^9)$, $C_5$–$C_6$-cycloalkyl or benzyl, at least one of the radicals $R^2$ and $R^3$ differing from hydrogen and it also being possible for $R^2$ and $R^3$ together to be $C_4$–$C_6$-alkylene or for $R^2$ and $R^1$ together to be $C_3$–$C_5$-alkylene, $R^4$ and $R^5$ independently of one another denote hydrogen or straight-chain or branched $C_1$–$C_4$-alkyl, which can be substituted by halogen, $R^6$ and $R^7$ independently of one another represent hydrogen, straight-chain or branched $C_1$–$C_{12}$-alkyl, straight-chain or branched $C_1$–$C_4$-alkoxy, phenyl, phenoxy, halogen, hydroxyl, nitro, cyano or $N(R^8,R^9)$, it being possible for $R^6$ additionally to denote $CON(R^8,R^9)$, $COR^8$ or $COOR^8$, and $R^8$ and $R^9$ independently of one another represent hydrogen or straight-chain or branched $C_1$–$C_4$-alkyl, wherein less than 5 equivalents, based on 1 mol of phenylhydrazine, of an acid compound having a pK value of 1.3–4.5 are employed, 2. The process of claim 1, wherein a phenylhydrazine having at least one unsubstituted orthoposition, of the formula

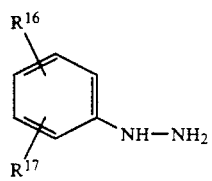

is employed, wherein

R$^{16}$ and R$^{17}$ independently of one another denote hydrogen, straight-chain of branched C$_1$-C$_{12}$-alkyl, straight-chain or branched C$_1$-C$_4$-alkoxy, phenyl, phenoxy, halogen, hydroxyl, cyano or N(R$^{18}$,R$^{19}$), R$^{18}$ and R$^{19}$ independently of one another representing hydrogen, methyl or ethyl.

3. The process of claim 2, wherein a phenylhydrazine having at least one unsubstituted ortho-position, of the formula

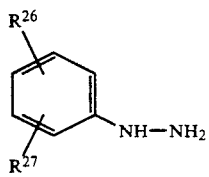

is employed, wherein

R$^{26}$ and R$^{27}$ independently of one another denote hydrogen, methyl, ethyl, methoxy, ehtoxy or halogen and R$^{26}$ additionally can denote hydroxyl or N(R$^{18}$,R$^{19}$).

4. The process of claim 1, wherein a ketone of the formula

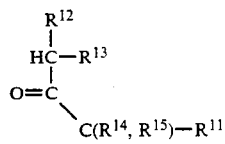

is employed, wherein

R$^{11}$ represents hydrogen or methyl or ethyl, each of which can be substituted by halogen, R$^{12}$ and R$^{13}$ independently of one another denote hydrogen, straight-chain or branched C$_1$-C$_4$-alkyl, which can be substituted by halogen, or benzyl, at least one of the radicals R$^{12}$ and R$^{13}$ differing from hydrogen, and R$^{14}$ and R$^{15}$ independently of one another denote hydrogen or methyl or ethyl, each of which can be substituted by halogen.

5. The process of claim 4, <wherein a ketone of the formula

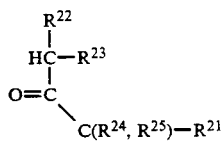

is employed, wherein

R$^{21}$, R$^{22}$, R$^{23}$, R$^{24}$ and R$^{25}$, independently of one another denote hydrogen or methyl or ethyl, each of which can be substituted by halogen, at least one of the radicals R$^{22}$ and R$^{23}$ differing from hydrogen.

6. The process of claim 1, wherein the acid compound having a pK value of 1.3 to 4.5 which is employed is an acid alkali metal salt, a weak inorganic acid or an organic acid in the indicated pK value range.

7. The process of claim 6, wherein the acid compound is an acid alkali metal salt.

8. The process of claim 7, wherein the acid compound is sodium hydrogen sulphate.

9. The process of claim 1, wherein 1–4.9 equivalents of the acid compound are employed per 1 mol of phenylhydrazine.

10. The process of claim 9, wherein 1.5–4.5 equivalents of the acid compound are employed per 1 mol of phenylhydrazine.

11. The process of claim 10, wherein 2–4 equivalents of the acid compound are employed per 1 mol of phenylhydrazine.

12. The process of claim 1, which is carried out at 50°–150° C.

13. The process of claim 12, which is carried out at 80°–110° C.

14. The process of claim 1, wherein a phenylhydrazine is employed which is prepared from the associated alkali metal phenylhydrazodisulphonate and/or the associated alkali metal phenylhydrazo-β-sulphonate in the presence of residual alkali metal sulphite and/or alkali metal hydrogen sulphite by addition or sulphuric acid.

15. The process of claim 14, wherein the amount of sulphuric acid is adjusted such that, from the residual alkali metal sulphite, alkali metal hydrogen sulphite and the sulphate eliminated from the hydrazosulphonate, in total less than 5 equivalents of acid compound in the form of hydrogen sulphate are present per mole of hydrazine.

16. The process of claim 14, wherein the elimination of the sulphonate group from the alkali metal phenylhydrazodisulphonate and/or the alkali metal phenylhydrazo-β-sulphonate is carried out in the presence of the ketone and the indole synthesis is carried out without intermediate isolation of the phenylhydrazine in this medium.

17. The process of claim 16, wherein an aniline having at least one unsubstituted ortho-position of the formula

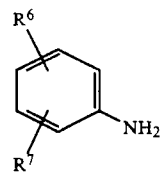

wherein

R$^6$ and R$^7$ independently of one another denote hydrogen, straight-chain or branched C$_1$-C$_{12}$-alkyl, straight-chain or branched C$_1$-C$_4$-alkoxy, phenyl, phenoxy, halogen, hydroxyl, nitro, cyano or N(R$^8$,R$^9$), it being possible for R$^6$ additionally to denote CON(R$^8$,R$^9$), COR$^8$ or COOR$^8$, is used as the starting material for the preparation of the indole and the reaction steps of diazotisation, reduction of the diazonium salt by means of sulphite, elimination of the sulphonate group and the final step of the reaction with the ketone are carried out without isolation of the intermediates.

* * * * *